(12) United States Patent
Talley

(10) Patent No.: US 8,978,998 B1
(45) Date of Patent: Mar. 17, 2015

(54) MOUNTABLE FRAGRANCE DISPENSER

(76) Inventor: Theresa A. Talley, McMinnville, TN (US)

( * ) Notice: Subject to any disclaimer, the term of this patent is extended or adjusted under 35 U.S.C. 154(b) by 575 days.

(21) Appl. No.: 13/349,846

(22) Filed: Jan. 13, 2012

(51) Int. Cl.
*A24F 25/00* (2006.01)
*A61L 9/12* (2006.01)

(52) U.S. Cl.
CPC .................................... *A61L 9/127* (2013.01)
USPC ........................................ 239/51.5; 239/55

(58) Field of Classification Search
CPC ........... A61L 9/12; A61L 9/14; F24D 19/008; A24F 25/02
USPC ................... 239/51.5, 53–58, 36, 34
See application file for complete search history.

(56) References Cited

U.S. PATENT DOCUMENTS

| 2,103,609 | A | | 12/1937 | Bradburn |
| 2,720,013 | A | * | 10/1955 | Clarke ............................ 43/129 |
| 4,094,639 | A | | 6/1978 | McMillan |
| 4,603,030 | A | | 7/1986 | McCarthy |
| 4,813,344 | A | * | 3/1989 | Greif ............................. 454/156 |
| 5,178,327 | A | | 1/1993 | Palamand et al. |
| 5,422,078 | A | * | 6/1995 | Colon ........................... 422/123 |
| 5,695,692 | A | | 12/1997 | Kennedy |
| 6,619,559 | B2 | | 9/2003 | Wohrle |

* cited by examiner

*Primary Examiner* — Davis Hwu
(74) *Attorney, Agent, or Firm* — Robert C. Montgomery; Montgomery Patent & Design

(57) ABSTRACT

A fragrance dispenser mountable to a fan includes a dispenser housing which retains a pair of removable air fragrance packs. The dispenser housing includes a plurality of air vent openings through a rear panel which promotes air flow through the interior of the dispenser housing and over the removable fragrance packs. A sliding door allows a user to selectively block and expose varying portions of the dispenser interior and thus corresponding fragrance packs. The dispenser also includes a pair of clips located along a rear surface which engage a grill of a fan or similar air distribution device. When the fan is activated, air flow caused by the fan circulates through the dispenser housing and over the fragrance pack dispensing a scent or air freshener to the surrounding area.

17 Claims, 5 Drawing Sheets

MOUNTABLE FRAGRANCE DISPENSER

RELATED APPLICATIONS

Not Applicable.

FIELD OF THE INVENTION

The present invention relates generally to air fresheners, and in particular, to an air freshener and fragrance dispenser which is mountable to an air distribution device.

BACKGROUND OF THE INVENTION

Keeping a room clean and fresh smelling is a never-ending battle in many homes and offices. Stale odors, poor circulation, tobacco smoke, food odors, and the like all combine to assault the olfactory senses of anyone entering a room. Various ways to combat these odors are known. They include the use of aerosol sprays, solid room deodorizers, and electric room deodorizers; all of which discharge some type of air freshening material into a room.

A common problem with all of these systems is that the freshening smell is overpowering at first and then the aroma quickly diminishes over time. Another problem area is that the freshening aroma is not evenly distributed around the room and is only concentrated in the area where it was released. Furthermore with all of these methods, a user is required to place and replace them on a consistent and regular basis in order to for them to be effective.

SUMMARY OF THE INVENTION

The inventor has recognized the aforementioned inherent problems and lack in the art and observed that there is a need for a mountable device for distributing air fragrances in an automatic and unattended manner.

Accordingly, it is an object of the present embodiments of the invention to solve at least one of these problems. The inventor has addressed this need by developing a mountable fragrance dispenser that provides effective control and masking of odors in a room in a manner which is quick, easy, and effective. The inventor has thus realized the advantages and benefits of providing a dispenser housing having a rear panel, a pair of side panels, a bottom panel, and a top panel defining a hollow interior with an open front. A plurality of fragrance packs is also provided. Each fragrance pack includes an open tray with an air freshening mechanism disposed within the tray for deodorizing or supplying a fragrance to a room. The top panel includes a pair of slots. Each slot is suitably sized for insertably receiving one (1) of the plurality of fragrance packs. A divider is provided that protrudes from an interior surface of the rear panel and extends centrally along a longitudinal axis thereof for separating the dispenser housing hollow interior into two (2) halves. The two (2) halves are aligned with the pair of slots for retaining the pair of fragrance packs. A plurality of openings is disposed traversly through the rear panel for providing an air flow into the hollow interior and over the air freshening mechanism of the fragrance packs. A door is slidably attached to the dispenser housing for selectably covering a portion of the open front between a first position and a second position. A rear extension protrudes from an upper exterior surface of the rear panel for providing a standoff distance between the fragrance packs and an air distribution device. At least one (1) spring clip is affixed to the rear extension for removably mounting the dispenser housing to the air distribution device. In use, when the door is in the first position, a first fragrance pack is uncovered and when the door is in the second position, a second fragrance pack is uncovered.

Furthermore, the described features and advantages of the disclosure may be combined in various manners and embodiments as one skilled in the relevant art will recognize. The disclosure can be practiced without one (1) or more of the features and advantages described in a particular embodiment.

Further advantages of the present disclosure will become apparent from a consideration of the drawings and ensuing description.

BRIEF DESCRIPTION OF THE DRAWINGS

The advantages and features of the present disclosure will become better understood with reference to the following more detailed description and claims taken in conjunction with the accompanying drawings, in which like elements are identified with like symbols, and in which:

DESCRIPTIVE KEY

Figure 1:
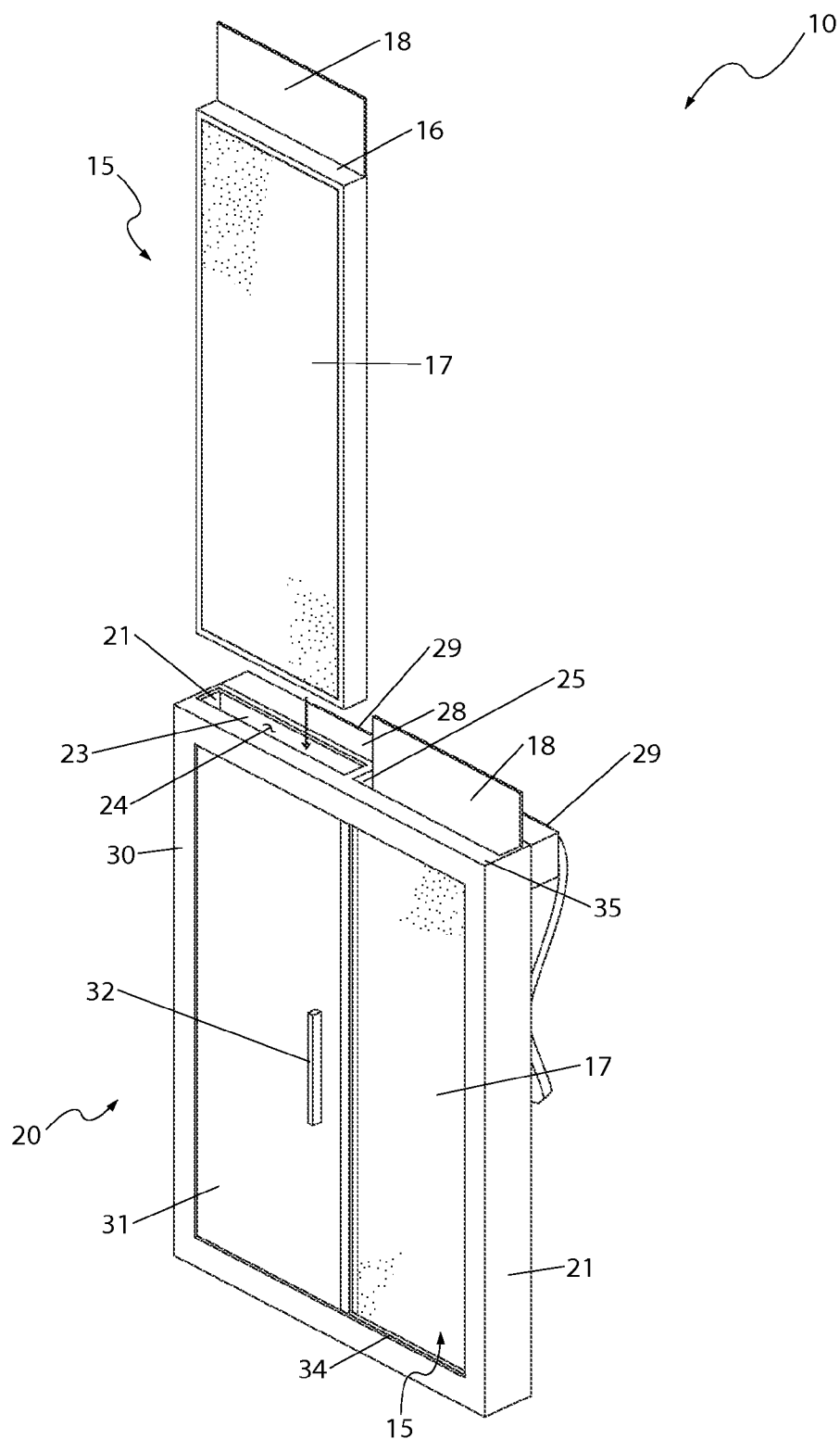
FIG. 1 is a perspective view of a mountable fragrance dispenser shown in an in use condition, in accordance with the invention.

10 mountable fragrance dispenser
11 air flow
15 fragrance insertion pack
16 tray
17 air freshening mechanism
18 tab
20 dispenser housing
21 side panel
22 bottom panel
23 rear panel
24 first slot
25 second slot
26 divider
27 opening
28 rear extension
29 clip
30 front opening
31 door
32 handle
33 upper channel
34 lower channel
35 top panel

DETAILED DESCRIPTION OF THE PREFERRED EMBODIMENT

In accordance with the invention, the best mode is presented in terms of a preferred embodiment, herein depicted within FIGS. 1 through 5. However, the disclosure is not limited to a single described embodiment and a person skilled in the art will appreciate that many other embodiments are possible without deviating from the basic concept of the disclosure and that any such work around will also fall under its scope. It is envisioned that other styles and configurations can be easily incorporated into the teachings of the present disclosure, and only one particular configuration may be shown and described for purposes of clarity and disclosure and not by way of limitation of scope.

The terms "a" and "an" herein do not denote a limitation of quantity, but rather denote the presence of at least one of the referenced items.

Referring now to FIGS. 1 through 4, depicting a mountable fragrance dispenser (herein described as an "apparatus") 10, where like reference numerals represent similar or like parts. In accordance with the invention, the present disclosure describes a dispensing apparatus 10 for providing an aromatic fragrance throughout an area to neutralize odors in an automatic and unattended manner.

FIG. 1 shows an in-use perspective view of the apparatus 10. The apparatus 10 includes a pair of fragrance insertion packs 11 and a dispenser housing 20. Each fragrance insertion pack 11 is insertable into the dispenser housing 20 and emits a pleasing scent throughout the area as air passes over the insertion pack 11. Each fragrance insertion pack 11 includes a tray 16 and an air freshening mechanism 17. In certain embodiments the air freshening mechanism 17 is an evaporative scented gel or similar material, as used in GLADE® PLUGINS®. The tray 16 is a shallow tray having enclosed sides, top and bottom and an open front and rear for retaining the air freshening mechanism 17. The tray 16 also includes a thin tab extending upwardly from the top for providing a graspable surface for insertion and removal of the fragrance insertion pack 11.

The air freshening mechanism 17 is preferably an impregnated gel which releases a fragrant aroma as it evaporates, however it can be appreciated that other air freshening mechanisms, such as packaged fragrance oils, can be utilized without limiting the scope of the apparatus 10. In various embodiments the air freshening mechanism 17 is fabricated having various different fragrances such as, but not limited to: sweet pea, vanilla, linen, and the like. Each fragrance insertion pack 11 is expected to last for weeks or months depending on usage and volume of air flow and is replaceable as needed. The air freshening mechanism 17 is purchased as a replaceable component of apparatus 10 separate from the dispenser housing 20. The dispenser housing 20 is adapted to attach to an electric fan, ceiling fan, HVAC register, or the like which allows the air freshening mechanism 17 to evaporate and emit a pleasing scent into the desired area.

Figure 2:
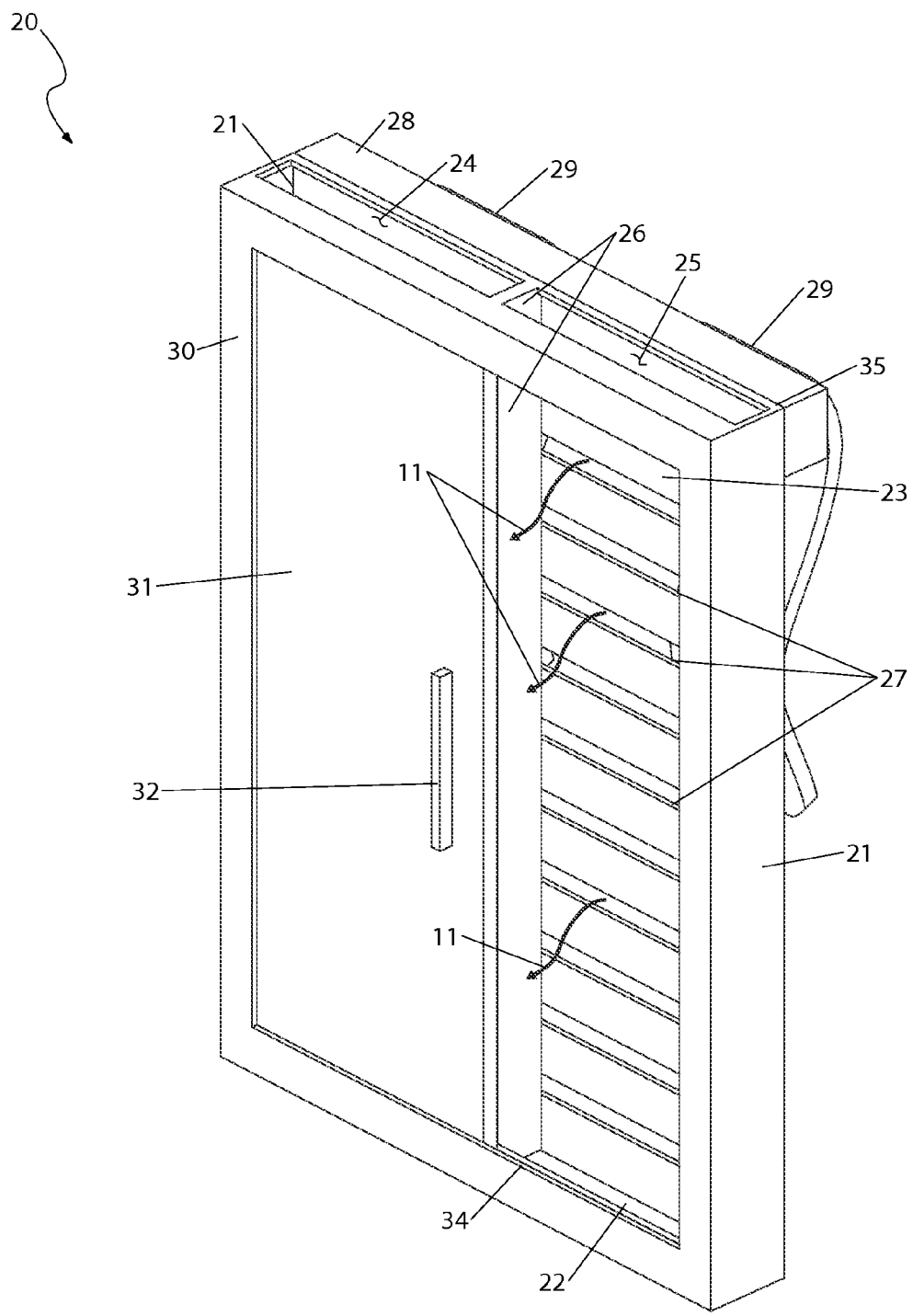
FIG. 2 is a front perspective view of the dispenser housing shown with a door in a first position.
Figure 3:
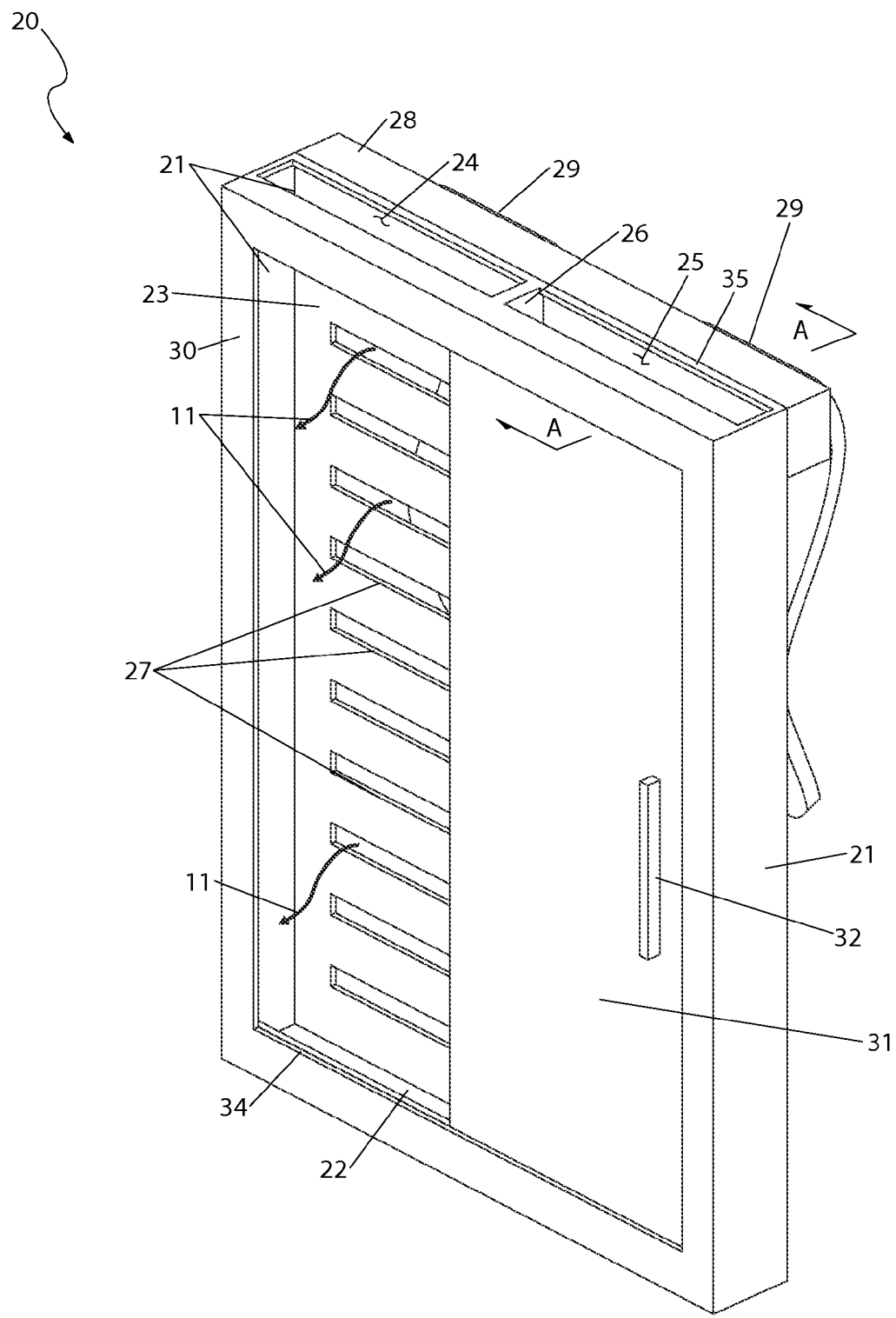
FIG. 3 is a front perspective view of the dispenser housing shown with the door in a second position.
Figure 4:
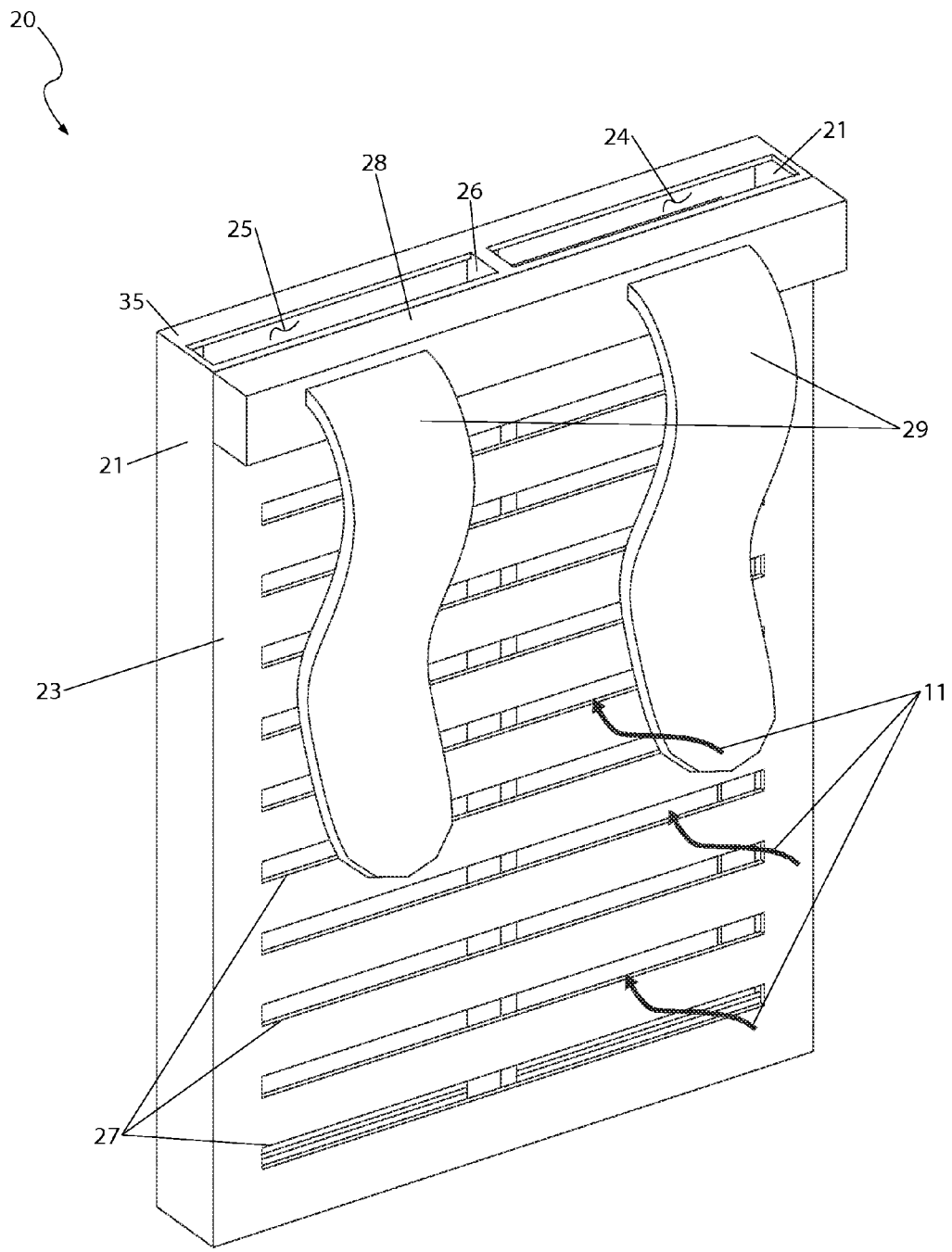
FIG. 4 is a rear perspective view of the dispenser housing.
Figure 5:
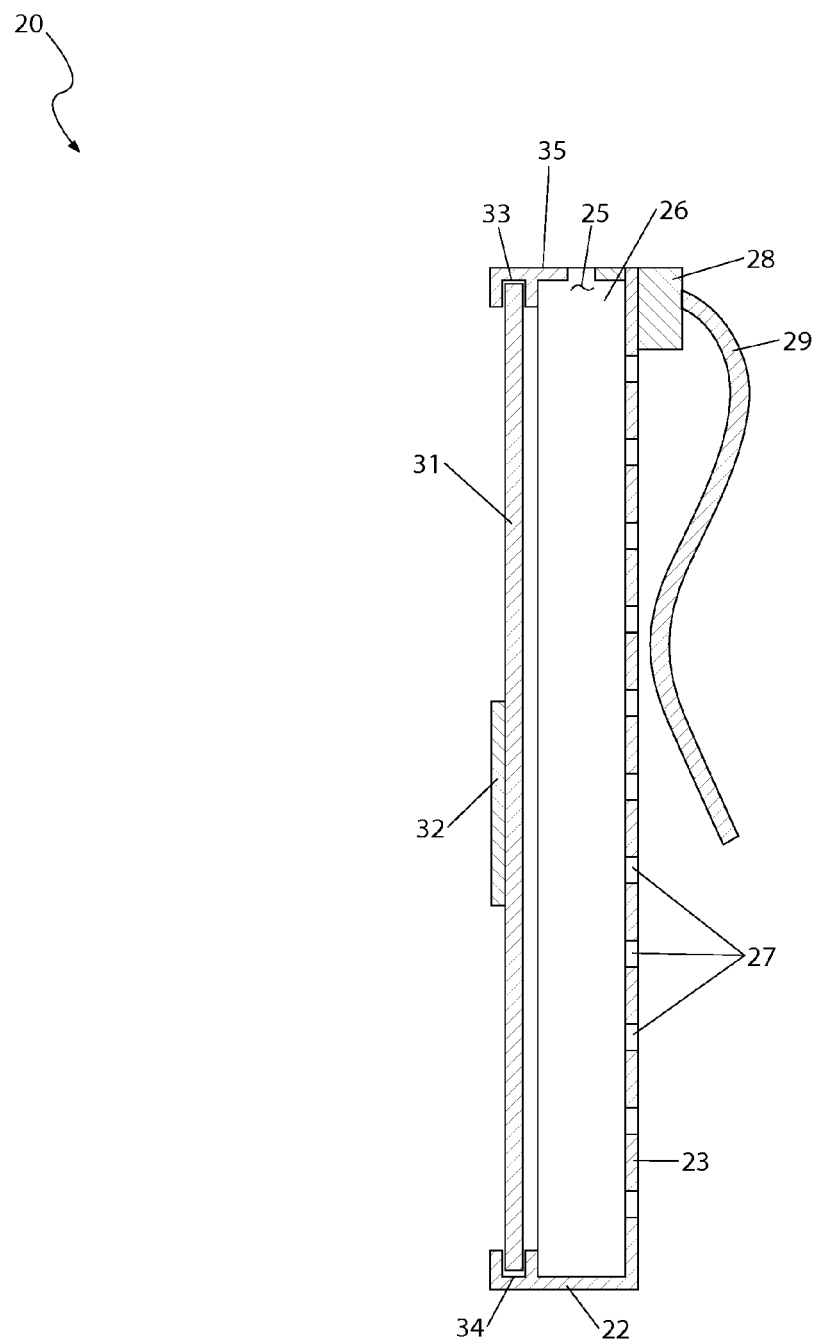
FIG. 5 is a section view of the dispenser housing taken along line A-A of FIG. 3.

FIG. 2 shows a front perspective view of the dispenser housing 20, FIG. 3 shows another front perspective view of the dispenser housing 20, FIG. 4 shows a rear perspective view of the dispenser housing 20, and FIG. 5 shows a section view of the dispenser housing 20 taken along line A-A of FIG. 3. The dispenser housing 20 retains a pair of fragrance insertion packs 15 and is attachable to a selected air dispersal device, such as a fan. Attachment of the apparatus 10 to the fan allows the air freshening mechanism 17 to be dispersed throughout the desired area as an air flow 11 passes over. The dispenser housing 20 has a generally rectangular shape which includes a pair of side panels 21, a bottom panel 22, a rear panel 23, a front opening 30, a top panel 35, and an interior panel 27 which are integrally molded from plastic, yet other materials can be utilized without limiting the scope of the apparatus 10.

The top panel 35 includes a first slot 24 and a second slot 25, each of which are adapted to receive a fragrance insertion pack 15 which is removably inserted into a hollow interior of the dispenser housing 20. The slots 24, 25 have dimensions slightly larger than the dimensions of the fragrance insertion packs 15. Once a fragrance insertion pack 15 is inserted into a selected slot 24, 25 it is retained within the side panel 21, the bottom panel 22, the rear panel 23, and a divider 26. The divider 26 extends longitudinally between the rear panel 23 and the open front and separates the interior into halves defining fragrance insertion pack retaining areas and bisects the front opening 30. The pair of fragrance insertion packs 15 is individually separated by the divider 26. The divider 26 is integrally molded to an inner surface of the bottom panel 22 and the rear panel 23 and spans the length of the rear panel 23 and the width of the bottom panel 22. The front opening 30 exposes the air freshening mechanism 17 to the area to be scented.

The dispenser housing 20 also includes an upper channel 33 and a lower channel 34 which retain and guide a door 31 which his slid to a desired position in order to expose a selected fragrance insertion pack 15. The lower channel 34 spans the length of the bottom panel 22 adjacent to a forward edge. The upper channel 33 spans the length of the top panel 35 adjacent to a forward edge. The door 31 includes a handle 32 which provides a grip for a user to manually move the door 31 within the channels 33, 34 to a first position or a second position, thereby exposing the selected fragrance insertion pack 15. The door 31 obstructs a corresponding half of the front opening 30 and respective subjacent unselected fragrance insertion pack 15 and exposes an opposing half of the front opening 30 and respective selected fragrance insertion pack 15.

The rear panel 23 includes a plurality of elongated openings 27 which allow air flow 11 to pass through the dispenser housing 20 and over the air freshening mechanism 17. The air flow 11 is provided by the electric fan, ceiling fan, HVAC register, or similar air dispersal device. The air flow 11 passed into the dispenser housing 20 and passes over the fragrance insertion pack 15 to disperse the scent throughout the desired area. The openings 27 are rectangular cut-outs oriented widthwise along the rear panel 23. It can be appreciated that other shapes and styles of openings can be utilized without limiting the scope of the apparatus 10.

An upper portion of the rear panel 23 also includes a rear extension 28 which provides a standoff gap between the dispenser housing 20 and the source of the air flow 11. A pair of clips 29 is affixed to an exterior of the rear extension 28. The clips 29 provide for the dispenser housing 20 to be attached to the source of the air flow 11. The clips 29 are fabricated from plastic or spring steel and preferably engage a grate or cover of the air dispersing device in order to suspend the apparatus 10 directly in front of the air flow 11.

It can be appreciated by one skilled in the art that other styles and configurations of the invention can be easily incorporated into the teachings of the present disclosure and only one particular configuration has been shown and described for purposes of clarity and disclosure and not by way of limitation of scope.

In accordance with the invention, the preferred embodiment can be utilized by the user in a simple and effortless manner with little or no training. After initial purchase or acquisition of the apparatus 10, it is installed and utilized as indicated in FIGS. 1 through 5.

The method of installing and utilizing the apparatus 10 can be achieved by performing a series of steps. It can be appreciated that the steps described can be performed in alternative order and as such should not be viewed as a limiting factor. Acquiring the apparatus 10 and suspending the dispenser housing 20 by the clips 29 from a desired device. Inserting a pair of fragrance insertion packs 15 into the slots 24, 25. Sliding the door 31 within the channels 33, 34 to a selected position to expose a selected air freshening mechanism 17 and obstruct the opposing air freshening mechanism 17. Providing the air flow 11 to disperse from the air dispersal device into the dispenser housing 20, over the fragrance insertion pack 15 and into the room area. Utilizing the apparatus 10 to effectively control and mask odors in a room.

The foregoing descriptions of specific embodiments have been presented for purposes of illustration and description. They are not intended to be exhaustive or to limit the invention and method of use to the precise forms disclosed. Various modifications and variations can be appreciated by one skilled in the art in light of the above teachings. The embodiments have been chosen and described in order to best explain the principles and practical application in accordance with the invention to enable those skilled in the art to best utilize the various embodiments with expected modifications as are suited to the particular use contemplated. It is understood that various omissions or substitutions of equivalents are contemplated as circumstance may suggest or render expedient, but is intended to cover the application or implementation without departing from the spirit or scope of the claims of the invention.

What is claimed is:

1. A mountable fragrance dispenser comprising:
    a dispenser housing comprising a hollow interior defined by a rear panel, a pair of side panels, a bottom panel, a top panel, and an open front;
    a plurality of openings disposed traversly through said rear panel for providing an air flow into said hollow interior;
    at least one fragrance pack insertable within said dispenser housing hollow interior, said fragrance pack comprising an open tray with an air freshening mechanism disposed within said tray; and,
    at least one spring clip affixed to said dispenser housing for removably mounting said dispenser housing to an air distribution device;
    wherein said dispenser housing further comprises a rear extension protruding from an upper exterior surface of said rear panel for providing a standoff distance between said fragrance packs and said air distribution device.

2. The apparatus of claim 1, wherein said air freshening mechanism further comprises an evaporative scented gel.

3. The apparatus of claim 1, wherein said rear panel further comprises a divider protruding from an interior surface and extending centrally along a longitudinal axis for separating said dispenser housing hollow interior into two halves, each of said halves for retaining said at least one fragrance pack.

4. The apparatus of claim 1, wherein said dispenser housing further comprises a slidably attached door for selectably covering a portion of said open front between a first position and a second position;
    wherein when said door is in said first position a first fragrance pack is uncovered and when said door is in said second position a second fragrance pack is uncovered.

5. The apparatus of claim 4, wherein said top panel further comprises an upper channel for receiving an upper end of said door and said bottom panel further comprises a lower channel for receiving a lower end of said door;
    wherein said door is slidable within said upper channel and said lower channel between said first position and said second position.

6. The apparatus of claim 4, wherein said door further comprises a handle protruding from an exterior surface.

7. The apparatus of claim 1, wherein said top panel further comprises a pair of slots, each slot being suitably sized for insertably receiving one fragrance pack.

8. The apparatus of claim 1, wherein said spring clip is affixed to said rear extension.

9. The apparatus of claim 1, wherein said fragrance pack tray further comprises a tab protruding from a top end for providing a graspable surface for inserting and removing said fragrance pack from said dispenser housing.

10. A mountable fragrance dispenser comprising:
    a dispenser housing comprising a rear panel, a pair of side panels, a bottom panel, and a top panel defining a hollow interior with an open front;
    a plurality of fragrance packs, each of said fragrance packs comprises an open tray with an air freshening mechanism disposed within said tray;
    a pair of slots disposed in said top panel, each of said slots being suitably sized for insertably receiving one of said plurality of fragrance packs;
    a divider protruding from an interior surface of said rear panel and extending centrally along a longitudinal axis for separating said dispenser housing hollow interior into two halves aligned with said pair of slots for retaining two of said plurality of fragrance packs;
    a plurality of openings disposed traversly through said rear panel for providing an air flow into said hollow interior and over said air freshening mechanism;
    a door slidably attached to said dispenser housing for selectably covering a portion of said open front between a first position and a second position;
    a rear extension protruding from an upper exterior surface of said rear panel for providing a standoff distance between said fragrance packs and an air distribution device; and,
    at least one spring clip affixed to said rear extension for removably mounting said dispenser housing to said air distribution device;
    wherein when said door is in said first position a first fragrance pack is uncovered and when said door is in said second position a second fragrance pack is uncovered.

11. The apparatus of claim 10, wherein said top panel further comprises an upper channel for receiving an upper end of said door and said bottom panel further comprises a lower channel for receiving a lower end of said door;
    wherein said door is slidable within said upper channel and said lower channel between said first position and said second position.

12. The apparatus of claim 10, wherein said fragrance pack tray further comprises a tab protruding from a top end for providing a graspable surface for inserting and removing said fragrance pack from said dispenser housing.

13. The apparatus of claim 10, wherein said door further comprises a handle protruding from an exterior surface.

14. The apparatus of claim 10, wherein said air freshening mechanism further comprises an evaporative scented gel.

15. The apparatus of claim 11, wherein said fragrance pack tray further comprises a tab protruding from a top end for providing a graspable surface for inserting and removing said fragrance pack from said dispenser housing.

16. The apparatus of claim 15, wherein said door further comprises a handle protruding from an exterior surface.

17. The apparatus of claim 16, wherein said air freshening mechanism further comprises an evaporative scented gel.

* * * * *